United States Patent [19]

Gilman

[11] Patent Number: 4,635,624

[45] Date of Patent: Jan. 13, 1987

[54] WOUND DRESSING

[75] Inventor: Thomas Gilman, Palatine, Ill.

[73] Assignee: The Kendall Company, Boston, Mass.

[21] Appl. No.: 734,301

[22] Filed: May 15, 1985

[51] Int. Cl.⁴ .............................................. A61L 15/00
[52] U.S. Cl. ................................................... 128/156
[58] Field of Search ................................ 128/156, 155

[56] References Cited

U.S. PATENT DOCUMENTS

| | | | |
|---|---|---|---|
| 2,233,209 | 2/1941 | Herzog | 128/156 |
| 2,785,677 | 3/1957 | Stumpf | 128/156 |
| 4,212,296 | 7/1980 | Schaar | 128/156 |
| 4,265,234 | 5/1981 | Schaar | 128/156 |
| 4,372,311 | 2/1983 | Potts | 128/156 |
| 4,413,621 | 11/1983 | McCracken | 128/156 |
| 4,499,896 | 2/1985 | Heinecke | 128/156 |

FOREIGN PATENT DOCUMENTS 0107915  5/1984  European Pat. Off. .

Primary Examiner—Gregory E. McNeill
Attorney, Agent, or Firm—Powell L. Sprunger

[57] ABSTRACT

A wound dressing comprising, a flexible base sheet having adhesive on a front surface thereof, and a back surface. The dressing has an absorbent pad. The dressing also has a flexible film defining a chamber to receive the pad, with the chamber overlying the back surface of the base sheet, and with the dressing having an opening extending through the adhesive and base sheet and communicating with the pad inside the chamber.

19 Claims, 8 Drawing Figures

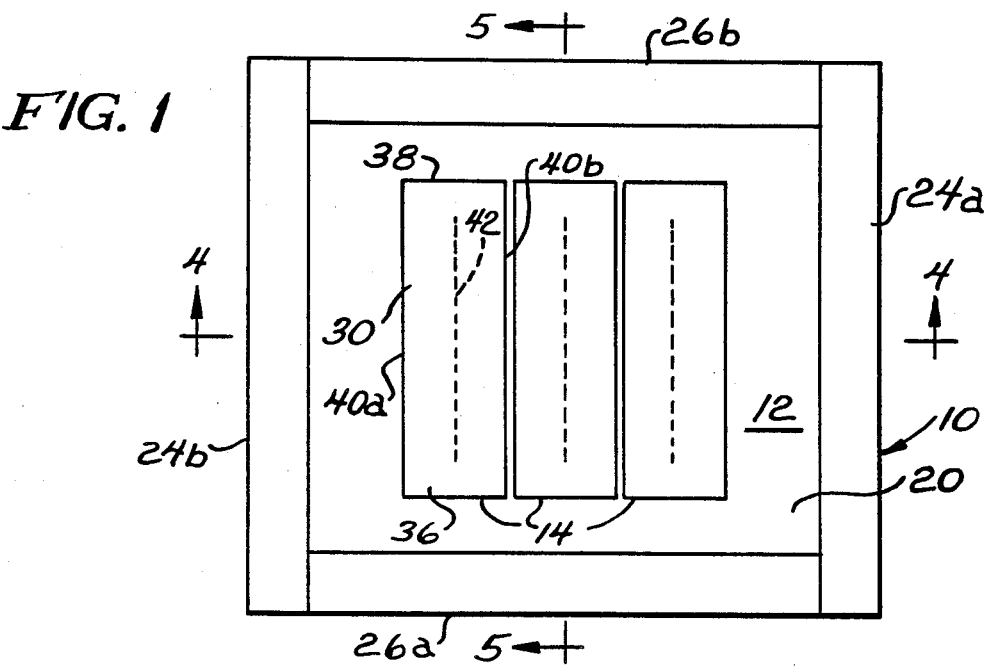
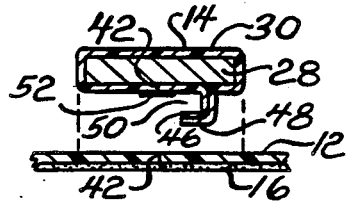 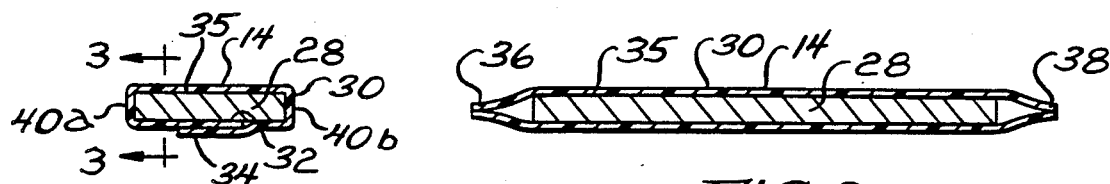
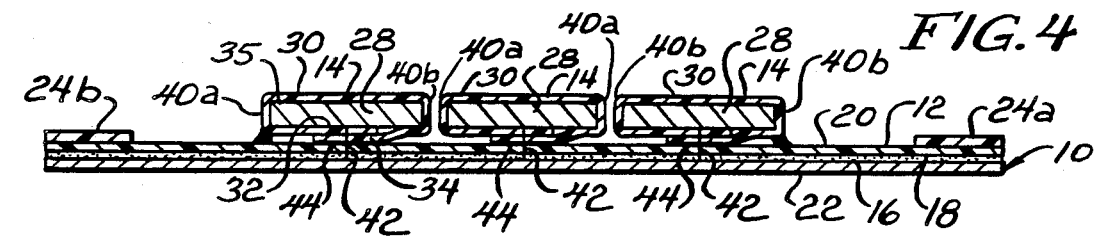
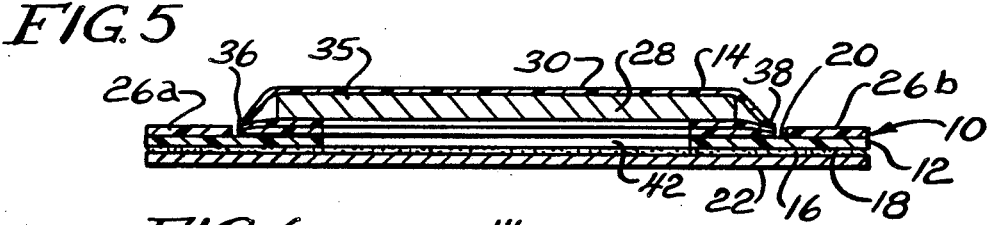
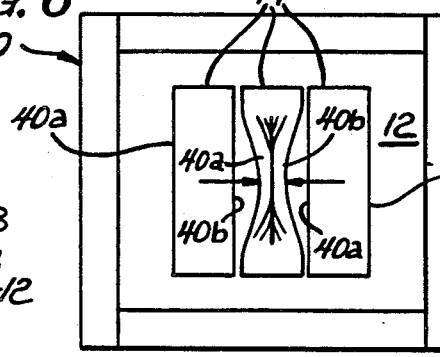
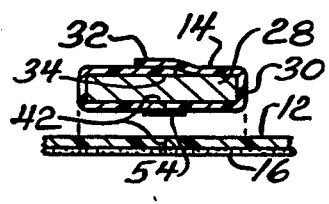

4,635,624

WOUND DRESSING

BACKGROUND OF THE INVENTION

The present invention relates to wound dressings.

Before the present invention, thin flexible films coated with adhesive have been sold to cover a wound. Such films are permeable to water vapor, and maintain the moist environment at the surface of the wound. The films also serve as a barrier to bacteria and outside contaminants. The films are transparent to inspect the wound without breaking the bacteria barrier to determine if a problem exists in the wound. However, such films have no capacity to handle wound fluids, and the fluids tend to undermine the adhesive resulting in possible breakage of the bacteria barrier and dislodgement of the film.

SUMMARY OF THE INVENTION

A principal feature of the present invention is the provision of an improved wound dressing.

The dressing of the present invention comprises, a flexible base sheet having adhesive on a front surface thereof, and a back surface. The dressing has an absorbent pad. The dressing also has a flexible film defining a chamber to receive the pad, with the chamber overlying the back surface of the base sheet, and with the dressing having opening means extending through the adhesive and base sheet and communicating with the pad inside the chamber.

A feature of the present invention is that the base sheet is transparent in order to inspect the wound without breaking the bacteria barrier defined by the base sheet.

Another feature of the invention is that the base sheet maintains a moist environment at the surface of the wound.

Another feature of the invention is that the fluids from the wound can drain through the opening means into the pad for absorption therein.

Yet another feature of the invention is that the dressing provides thermal insulation for the wound.

A further feature of the invention is that the dressing cushions the wound and protects it from mechanical trauma.

Still another feature of the invention is that the dressing prevents fluid of the wound from undermining the adhesive which otherwise might tend to break the bacteria barrier defined by the base sheet and possibly dislodge the dressing.

Further features will become more fully apparent in the following description of the embodiments of this invention and from the appended claims.

DESCRIPTION OF THE DRAWINGS

In the drawings:

FIG. 1 is a plan view of a wound dressing of the present invention;

FIG. 2 is a sectional view of a closed chamber for the dressing of FIG. 1;

FIG. 3 is a sectional view taken substantially as indicated along the line 3—3 of FIG. 2;

FIG. 4 is a sectional view taken substantially as indicated along the line 4—4 of FIG. 1;

FIG. 5 is a sectional view taken substantially as indicated along the line 5—5 of FIG. 1;

FIG. 6 is a plan view illustrating movement of closed chambers in order to inspect the wound under the dressing;

FIG. 7 is another embodiment of the dressing of the present invention; and

FIG. 8 is another embodiment of the dressing of the present invention.

DESCRIPTION OF THE PREFERRED EMBODIMENTS

Referring now to FIGS. 1, 4, and 5, there is shown a wound dressing generally designated 10 having a base sheet 12 of flexible transparent material, such as polyurethane, and a plurality of closed chambers 14 secured to the base sheet 12, as will be described below. In a preferred form, the dressing 10 has three closed chambers 14, as shown. The base sheet 12 has an adhesive 16 extending completely across a front surface 18 of the base sheet 12, and the base sheet 12 has a back surface 20. The dressing 10 has a release sheet 22 of known material which is releasably attached to and covers the adhesive 16. The base sheet 12 has a pair of strips 24a and 24b secured along opposed ends of the base sheet 12 on the back surface 20, and a pair of strips 26a and 26b extending along opposed sides of the base sheet 12 on the back surface 20. The strips 24a and b and 26a and b provide stiffness for the base sheet 12 during use of the dressing 10. The base sheet 12 is permeable to water vapor, and when secured by the adhesive 16 over a wound, maintains a moist environment at the surface of the wound. The base sheet 12 also provides a barrier to bacteria and outside contaminants when secured over a wound. Also, the base sheet is transparent in order to inspect the wound without breaking the bacteria barrier in order to determine whether there is a problem in the wound, as will be discussed below.

With reference to FIGS. 1–3, the closed chambers 14 include elongated pads 28 of an absorbent material, such as a needle punched polyester blend. An elongated film 30 of flexible material is wrapped about the pads 28 and having overlapping ends 32 and 34 in regions on the under surface of the pads 28, with the ends 32 and 34 being heat sealed together throughout the overlapped regions and with the wrapped films 30 defining cavities 35 to receive the pads 28. The length of the films 30 is greater than the length of the pads 28, such that the films 30 extend past the opposed ends of the pads 28. The opposed ends 36 and 38 of the films 30 are heat sealed together in order to close the films 30 in wrapped relationship about the pads 28. The films 30 and base sheet 12 may be made from a suitable material such as PEBAX, a polyether block amide, such as a material sold by Atochem, a French company from Paris, France. Such a film is thermoplastic in order to accomplish the heat sealing, and is highly permeable to water vapor and oxygen for use in the dressing 10. After the pads 28 have been wrapped by the films 30, the closed chambers 14 define elongated opposed side edges 40a and 40b.

With reference to FIGS. 4 and 5, the closed chambers 14 are heat sealed to the back surface 20 of the base sheet 12 in lateral central longitudinally extending zones 44 in the regions of the overlapping ends 32 and 34 of the films 30. Also, the outer ends 36 and 38 of the films 30 are heat sealed to the back surface 20 of the base sheet 12. Next, opening means, such as elongated slits 42, are formed through the adhesive 16, base sheet 12, and wrapped ends 32 and 34 in the zones 44 where the closed chambers 14 are heat sealed to the base sheet 12, such that the slits 42 communicate with the pads 28 in the closed chambers 14. Of course, different types of openings may be formed in the heat sealed zones, such as a plurality of aligned slits in the zones 44, or separate spaced openings located along the length of the heat sealed zones 44. The three sealed closed chambers 14 secured to the base sheet 12 are arranged in a side-by-side or contiguous relationship. In a preferred form, the left side edge 40a of the outermost left hand closed chamber 14, as viewed in FIG. 4, and the right side edge 40b of the outermost right hand closed chamber 14, as viewed in FIG. 4, are heat sealed to the back surface 20 of the base sheet 12 in order to prevent snagging of these closed chambers 14 during use of the dressing 10.

In use, the release sheet 22 is peeled from the adhesive 16 in order to expose the adhesive 16 and secure the base sheet 12 over a wound. During use of the dressing in this configuration, the base sheet 12 is permeable to water vapor, and maintains a moist environment at the surface of the wound, while also providing a complete barrier to bacteria and outside contamination. Also, the wound fluids may pass through the slits 42 extending through the adhesive 16, base sheet 12, and wrapped ends 32 and 34 of the films 30 into the absorbent pads 28 for retention therein. In this manner, the fluids from the wound are removed from the wound in order to prevent the fluids from undermining the adhesive 16 which otherwise might tend to break the bacteria barrier and dislodge the dressing 10. With reference to FIG. 6, when it is desired to inspect the wound, the side edges 40a and 40b of the central closed chamber 14 are moved by the fingers toward each other, and the wound may be inspected through the exposed portion of the base sheet 12. Of course, the side edge 40a of the right hand closed chamber 14, as viewed in FIG. 6, may be moved away from its normal position, or the side edge 40b of the left hand closed chamber 14, as viewed in FIG. 6, may be moved away from its normal position in order to inspect the wound.

Another embodiment of the dressing 10 of the present invention is illustrated in FIG. 7, in which like reference numerals designate like parts. In this embodiment, the closed chamber 14 also has a film 30 wrapped about a pad 28. The film 30 has extending ends 46 and 48 which are folded back together and sealed to the underlying portion of the film 30 in a region 50. The under surface of the film 30 is sealed to the base sheet 12 in a longitudinally extending zone 52 which is spaced from the ends 46 and 48. The slit 42 extends through the adhesive 16, base sheet 12, and sealed zone 52 for passage of fluids into the closed chamber 14.

Another embodiment of the present invention is illustrated in FIG. 8, in which like reference numerals designate like parts. In this embodiment, the overlapping ends 32 and 34 are secured together above an upper part of the pad 28. The closed chamber 14 is secured to the base sheet 12 in a longitudinally extending zone 54 spaced from the ends 32 and 34 beneath the pad 28, and the slit 42 extends through the adhesive 16, base sheet 12, and film 30 in the zone 54.

In alternative form, the base sheet 12 may be partially wrapped around the pads 28, with the ends of the wrapped sheet being secured together, and with the wrapped sheet defining openings beneath the pads 28.

The foregoing detailed description is given for clearness of understanding only, and no unnecessary limitations should be understood therefrom, as modifications will be obvious to those skilled in the art.

I claim:
1. A wound dressing, comprising:
    a flexible base sheet having adhesive on a front surface thereof, and a back surface;
    an absorbent pad; and
    a flexible film defining a chamber to receive the pad, with the chamber overlying the back surface of the base sheet, said dressing having opening means extending through the adhesive and base sheet and communicating with the pad inside the chamber.
2. The dressing of claim 1 wherein the base sheet comprises polyurethane.
3. The dressing of claim 1 wherein the sheet is permeable to water vapor.
4. The dressing of claim 1 wherein the film is permeable to water vapor.
5. The dressing of claim 1 wherein the film is permeable to oxygen.
6. The dressing of claim 1 wherein the pad comprises a needle punched polyester blend.
7. The dressing of claim 1 wherein the base sheet comprises polyether block amide.
8. The dressing of claim 1 wherein the film comprises polyether block amide.
9. A wound dressing, comprising:
    a flexible base sheet of transparent material having adhesive on a front surface thereof, and a back surface;
    an absorbent pad; and
    a flexible film enclosing the pad and defining a chamber to receive the pad, said film being secured in an area to the back surface of the base sheet, said dressing including opening means extending through the adhesive, base sheet and the film in said area such that the opening means communicates with said chamber.
10. The dressing of claim 9 wherein the film is overlapped in ends about the pad, and in which the overlapping ends are secured together in a region.
11. The dressing of claim 10 wherein said securement area is in said region.
12. A wound dressing, comprising:
    a flexible base sheet of transparent material having an adhesive on a front surface thereof, and a back surface;
    a plurality of absorbent pads; and
    a plurality of flexible films each enclosing a pad and defining a chamber, said films being secured in separate areas to the back surface of the sheet in a contiguous relationship, with the wrapped films having edges facing toward each other, and with the areas being spaced from at least a portion of adjacent edges, said dressing having opening means extending through the adhesive, base sheet and films in said areas such that the opening means communicates with the chambers.
13. A wound dressing, comprising:
    a flexible base sheet of transparent material having an adhesive on a front surface thereof, and a back surface;
    an elongated absorbent pad; and
    an elongated film of flexible material, said film being wrapped about the pad and having overlapping edges, with the edges being secured together in a region along the length of the film, with the film having a greater length than the length of the pad, and with the ends of the film being secured together and being closed, said film being secured to the back surface of the sheet in the region of the secured edges, said dressing having opening means extending through the adhesive, base sheet and film in the region of the secured edges.

14. A wound dressing, comprising:
a flexible base sheet of transparent material having an adhesive on a front surface thereof, and a back surface;
a plurality of elongated absorbent pads; and
a plurality of flexible films defining a closed chamber to receive the pads, with each closed film defining elongated side edges, with the length of the films being greater than the length of the pads and the ends of the films secured together and closed, said closed pads being secured to the back surface of the sheet with the side edges of each closed pad being adjacent each other, with the films being secured to the back surface of the sheet in lateral central longitudinally extending zones, said dressing having opening means extending through the adhesive, base sheet, and film in said zones such that the opening means communicates with the chambers.

15. The dressing of claim 14 wherein the opening means comprises elongated slits in said zones.

16. The dressing of claim 14 wherein the ends of the film are secured to the sheet.

17. The dressing of claim 14 wherein the outer side edges of the films for the outer closed chambers are secured to the sheet.

18. A wound dressing, comprising:
a flexible base sheet of transparent material having an adhesive on a front surface thereof, and a back surface;
an elongated absorbent pad; and
an elongated film of flexible material, said film being wrapped about the pad and having extending ends, with the ends being secured together and to an underlying portion of the film along the length of the film, said film being secured to the back surface of the sheet in a longitudinally extending zone spaced from the edges, said dressing having opening means extending through the adhesive, base sheet and film in said zone.

19. A wound dressing, comprising:
a flexible base sheet of transparent material having an adhesive on a front surface thereof, and a back surface;
an elongated absorbent pad; and
an elongated film of flexible material, said film being wrapped about the pad and having overlapping ends, with the ends being secured together along the length of the film, said film being secured to the back surface of the base sheet in a longitudinally extending zone spaced from the ends, said dressing having opening means extending through the adhesive, base sheet and film in said zone.

* * * * *